(12) United States Patent
Bookbinder et al.

(10) Patent No.: US 6,391,655 B1
(45) Date of Patent: May 21, 2002

(54) OXIDIZED STYRENIC POLYMERS FOR DNA BINDING

(75) Inventors: Dana C. Bookbinder, Corning; Leroy S. Hersh; Xinying Xie, both of Painted Post, all of NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 09/124,352

(22) Filed: Jul. 29, 1998

Related U.S. Application Data (60) Provisional application No. 60/054,256, filed on Jul. 30, 1997.

(51) Int. Cl.[7] .......................... G01N 33/545; C12Q 1/68

(52) U.S. Cl. .......................................... 436/531; 435/6

(58) Field of Search ............................ 436/531; 435/6; 530/391.1

(56) References Cited

U.S. PATENT DOCUMENTS

| | | | |
|---|---|---|---|
| 3,115,418 A | | 12/1963 | Magat et al. .................. 117/47 |
| 4,351,824 A | | 9/1982 | Lehrer .......................... 424/12 |
| 4,933,410 A | * | 6/1990 | Okrongly |
| 4,994,373 A | | 2/1991 | Stavrianopoulos et al. ..... 435/6 |
| 5,118,800 A | | 6/1992 | Smith et al. ................... 536/23 |
| 5,143,854 A | | 9/1992 | Pirrung et al. .............. 436/518 |
| 5,281,660 A | * | 1/1994 | Bryhan et al. |
| 5,414,075 A | | 5/1995 | Swan et al. .................. 568/333 |
| 5,474,895 A | * | 12/1995 | Ishii et al. |
| 5,510,481 A | | 4/1996 | Bednarski et al. ........... 536/120 |
| 5,552,280 A | | 9/1996 | Urdea et al. .................... 435/6 |
| 5,556,748 A | | 9/1996 | Douglas ......................... 435/6 |
| 5,610,287 A | | 3/1997 | Nikiforov et al. .......... 536/24.3 |
| 5,919,626 A | * | 7/1999 | Shi et al. |
| 5,945,319 A | * | 8/1999 | Keogh |

FOREIGN PATENT DOCUMENTS

| | | |
|---|---|---|
| EP | 0 155 252 | 9/1985 |
| EP | 0 390 500 A3 | 10/1990 |
| EP | 0 420 260 | 4/1991 |
| WO | WO 91/02768 | 3/1991 |

OTHER PUBLICATIONS

M. Zouali and B. D. Stollar, Jan. 24, 1986, "A rapid ELISA for measurement of Antibodies to nucleic acid antigens using UV–treated polystyrene microplates", Journal of Immunological Methods, pp. 105–110.

Corning Science Products 1998/1999 Catalog, pp. 80 & 81, Surface Selection Guide.

Moncef Zouali and B. David Stollar, "A rapid ELISA for measurement of Antibodies to nucleic acid antigens using UV–treated polystyrene microplates", Journal of Immunological Methods, 90(1986) pp. 105–110.

E. Engvall, "Determination of Antibodies to DNA by ELISA", The Lancet, Dec. 25, 1976, p. 1410.

T. Hataya et al., "A PCR–Microplate Hybridization Method For Plant Virus Detection", Journal of Virological Methods, 1994, vol. 46, pp. 223–236.

* cited by examiner

*Primary Examiner*—Mary E. Ceperley
(74) *Attorney, Agent, or Firm*—Thomas R. Beall

(57) ABSTRACT

A method of immobilizing aminated DNA to a substrate surface is provided for use in DNA hybridization assays. The surface can be widely employed in a variety of molded laboratory products including multiwell plates, cell culture dishes, and biological containers. The method comprises the steps of providing a polystyrene substrate having a surface content of between 0.3 and 4.0% atomic percent oxygen, and attaching amine modified oligonucleotide to the surface of the substrate. A resultant product comprising a polystyrene substrate having a surface oxygen content of between 0.3 and 4.0% atomic percent, and a plurality of amine modified oligonucleotides directly attached to the surface of the substrate, is also disclosed.

12 Claims, 7 Drawing Sheets

FIG. 2

Comparison of DNA-Bind Surface
with Medium Bind PS for DNA Binding

FIG. 4

Effect of pH on DNA Binding

Comparison of 0.6 kb dsDNA (0.1 ng/ul)
Binding on M - B and NOS Surfaces

FIG. 7

Comparison of Oligo Binding
on Clear and Black Reactive PS

FIG. 8

OXIDIZED STYRENIC POLYMERS FOR DNA BINDING

This application claims benefit of PROVISIONAL APPLICATION Ser. No. 60/054,256 filed Jul. 30, 1997.

FIELD OF THE INVENTION

The invention relates to laboratory ware for chemical and biological testing and experimentation and, more specifically, to a surface that will immobilize DNA.

BACKGROUND OF THE INVENTION

Polymers have been widely utilized as vessels for cell culture, biological testing, medical research and other uses. Certain polymers such as styrenic polymers and more specifically, polystyrene, are optimal for use as substrates in specialty products for biological testing, and are typically employed. Polystyrene, for example, is cheap, optically clear, and may be processed at low temperatures.

Direct immobilization of DNA to a substrate surface has many applications to a variety of assay systems in molecular biology, such as immuno-PCR or detection of nucleic acids with specifically labeled probes, i.e. target capture hybridization. Target capture hybridization relies on immobilizing capture oligonucleotide molecules (usually single strand DNA or RNA fragments that may be isolated from a natural source, or produced by standard molecular biological techniques, having from about two to forty nucleotides) on a support surface and then hybridizing labeled complementary target DNA strands to the immobilized molecules.

An aminated nucleic acid molecule is said to be "immobilized" to a solid support if it is either adsorbed to the support, or covalently bonded thereto, with sufficient strength that it cannot be removed from the support by washing with water or an aqueous buffer. A certain release of capture oligonucleotides invariably occurs with systems employing adsorption as the method of attachment. Therefore, covalent bonding of the oligonucleotide is preferred.

One method of immobilizing aminated DNA by covalent bonding involves attaching dialdehyde starch (DAS) or N-oxysuccinimide esters (NOS) to a polymer surface. In surfaces having a DAS coating, the $NH_2$ that is attached to the aminated capture oligonucleotide covalently links to an aldehyde group from the DAS, thereby immobilizing the oligonucleotide molecule to the polystyrene surface via the coating. A method of attaching DAS to the surface of a cell culture plate is disclosed in U.S. Pat. Nos. 5,563,215 and 5,281,660.

With a NOS coating, DNA with primary amines added synthetically or by in-vitro manipulation can be directly coupled to the NOS surface. When the primary amines react with NOS groups at a slightly alkaline pH, the ester undergoes nucleophilic substitution as the amine attacks the carbonyl group and displaces the N-oxysuccinimide group. The specificity of this reaction creates the immobilization effect.

Another technique for immobilizing DNA to a substrate surface is by covalently grafting secondary amines to a polystyrene surface. In this technique, the oligonucleotide is first phosphorylated at the 5' end with polynucleotide kinase and ATP. The phospholated DNA is then coupled to the secondary amines on the surface using carbodiimide for 5 hours at 50°. The DNA is thereby immobilized by a phosphoramidate bond.

A problem exists with surface treatment involving coatings such as DAS or NOS, and with attaching secondary amines. With time, or when subjected to various environmental stresses, the surface becomes unstable and the immobilization characteristics of the attached coating are diminished. Further, the coupling efficiency of binding aminated DNA to such treated plates is quite low, less than 0.1%. Also, the surface treatment of the polymer substrate adds an additional step to the manufacturing process and adds cost to the final product.

The present invention provides a method of using a product that is made of relatively pure polystyrene that covalently binds aminated DNA. The product works as well as substrates that have been treated with DAS or NOS, but without the cost of adding a coating. The present invention can also be subjected to a variety of environmental stresses without losing any of its immobilizing characteristics. Additionally, since the product of present invention is reactive toward amine groups in general, it is capable of binding peptides and low molecular weight antigens for immunoassays, as well as antibodies, cell attachment factors and other bioreactive molecules.

SUMMARY OF THE INVENTION

The present invention provides a method of immobilizing aminated DNA to a substrate surface. The surface can be widely employed in a variety of molded laboratory products including multiwell plates, cell culture dishes, and biological containers. The method comprises the steps of providing a polystyrene substrate having a surface content of between 0.3 and 4.0 atomic percent oxygen, and attaching amine modified oligonucleotide to the surface of the substrate. A resultant product comprises a polystyrene substrate having a surface oxygen content of between 0.3 and 4.0 atomic percent, and a plurality of amine modified oligonucleotides directly attached to the surface of the substrate.

DETAILED DESCRIPTION OF THE INVENTION

The present invention results from an accidental discovery by the inventors. A study was conducted by the inventors to investigate the mechanisms involved in binding aminated DNA to various surfaces. Aminated DNA refers to a DNA oligimer that has been modified by addition of a primary amine attachment on a terminal end. The inventors used polystyrene multiwell strips coated with both NOS and DAS and the results were to be compared to an uncoated polystyrene strip of wells which was to serve as the control. "Multiwell strips" or "strip of wells" consist of a number of wells (typically 8), of the type which comprise the wells in multiwell plates, which are attached to each other to form a linear array. U.S. Pat. No. 3,649,464 shows a multiwell plate and U.S. Pat. No. 5,084,246 shows a multiwell strip. To the amazement of the inventors, the uncoated, untreated control strips bound the DNA as well as the treated strips. The inventors then began work to derive an explanation for this seemingly anomalous result. As a first step, they noted that all other studies that used untreated polystyrene controls were performed using multiwell plates instead of well strips, and no significant binding had been detected on the plates.

Having made this observation, the inventors then embarked on a study to compare various substrate surfaces to determine their ability to bind aminated DNA. The substrates they selected were: (1) plain, untreated polystyrene plates and strips, sold under the tradename "MEDIUM BIND" available from Corning Costar Corporation, (2) polystyrene plates and strips that had been subjected to 3 mRads of gamma radiation, sold under the tradename "HIGH BIND" available from Corning Costar Corporation, (3) polystyrene plates and strips coated with NOS, and (4) tissue culture plates made of polystyrene that had been subjected to Corona discharge. It should be noted that the tradenames "HIGH BIND" and "MEDIUM BIND" refer to the product's propensity for binding protein in ELISA assays; it does not refer to ability to bind aminated DNA.

The procedure used for colorimetric detection of biotinylated DNA as used to obtain the data on binding was as follows:

1. To the plate or strip, 100 ul/well of amine modified probe oligonucleotide in oligo binding buffer (50 mM $Na_2PO_4$, pH 8.5, 1 mM EDTA) was added. The combination was either incubated overnight at 4° C. or for 1 hour at 37° C.

2. Uncoupled oligonucleotide was removed by washing the plate three times with PBS.

3. The unreacted active groups were blocked by adding 200 ul/well of 3% BSA in oligo binding buffer. The plate or strip was then incubated for 30 minutes at 37° C. and then decanted.

4. 100 ul/well of hybridization solution containing the target nucleic acid was then added. The plate or strip was then incubated for 1 hour at 49° C.

5. The wells were washed with preheated 2×SSC (3.0M NaCl; 0.3M sodium citrate, pH 7.0) 0.1% SDS twice and soaked for 5 minutes at 49° C.

6. 100 ul/well of blocking solution containing streptavidin-peroxidase conjugate diluted 1:1000 was added. The plate or strip was incubated for 30 min. at 37° C.

7. The wells were washed three times with PBS.

8. 100 ul/well of fresh substrate solution was added. OD readings were taken at 405 nm at 10, 20, and 30 minutes. The OD readings were uncorrected for background absorbence.

Figure 1:
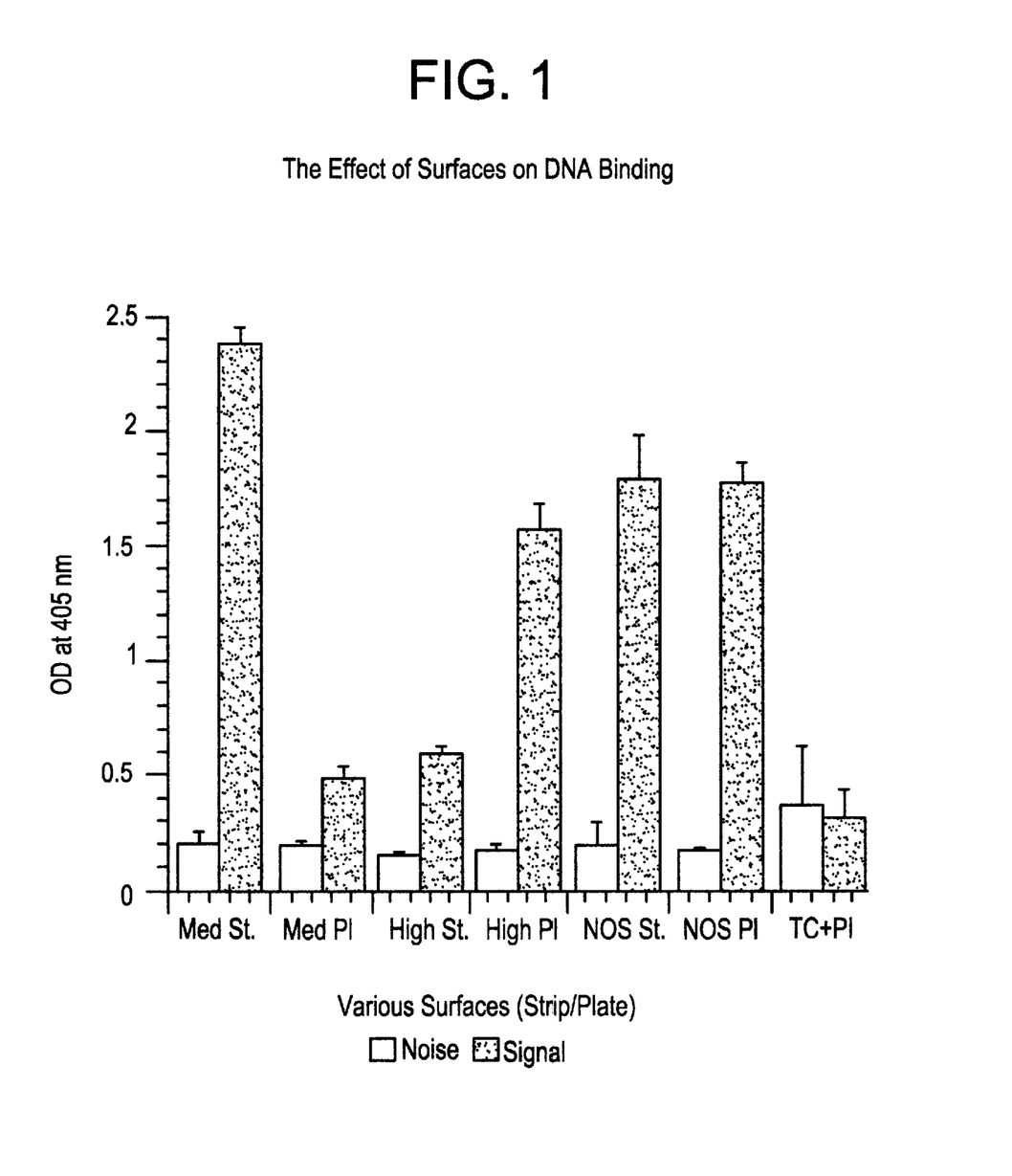
FIG. 1 is a graph of the effect that various surfaces have on binding aminated DNA.

In the experiment that yielded the results shown in FIG. 1, aminated DNA was applied to plates at a concentration of 1.0 pmol/well and incubated for 1 hour at 37° C. The results were recorded 20 minutes after adding fresh substrate solution. The readings that were taken are averages of readings from four different wells. Noise is a reading taken without DNA probes attached, signal is a reading measured with DNA probes. The background noise readings were obtained by following all the above listed preparation steps, but without adding any probe DNA. By subtracting this noise level from the signal obtained when probe DNA was added, all non-specific binding signal can be eliminated and a true measure of the binding effectiveness can be obtained.

As can be observed from FIG. 1, the untreated polystyrene strips (Med St.) bound the aminated DNA more effectively than the untreated plate (Med Pl.) or any of the treated surfaces.

Figure 2:
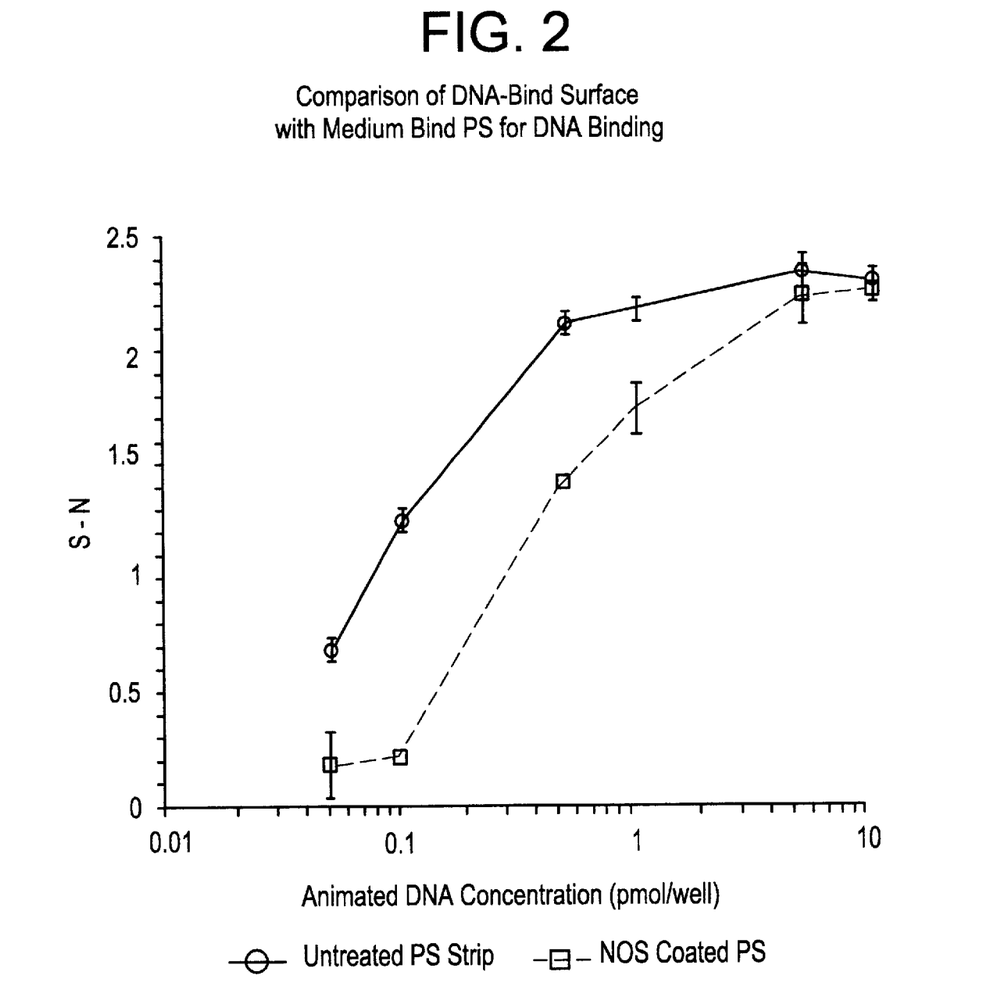
FIG. 2 is a graph comparing the binding effects of NOS coated polystyrene with the binding effects of an untreated polystyrene strip.

As a further illustration, an experiment was performed the results of which are displayed in FIG. 2. Aminated DNA was applied to NOS coated polystyrene plates and untreated polystyrene strips at various concentrations in oligo binding buffer (for NOS coated plates, pH 8.5, 1M NaCl, 50 mM phosphate, 1 mM EDTA; for untreated strips, 0.1M phosphate, pH 11.0) and incubated for 1 hour at 37° C. The values were obtained 20 minutes after adding substrate solution by averaging four wells and reading the OD at 405 nm. As the results show, the untreated polystyrene strip exhibits more signal, especially at lower concentrations, and therefore better binding characteristics than the NOS coated surface under these conditions.

The inventors next sought to determine what was different about the untreated strips when compared to the untreated plates from the same polystyrene. It was observed that the multiwell strips used in the experiment were produced by a molding process that was slightly different than the molding process used in the formation of the multiwell plate. For one, in molding the strips, no lubricant was used in the molds. Conversely, the molding of a plate requires lubricant, such as zinc stearate, in the mold cavity for proper ejection of the ware. Second, the mold for the strip uses more air venting than molds for the plates. With this in mind, the inventors began to look closely at the surface chemistry of both the untreated strips and plates, and more specifically, the surface oxygen content of the polystyrene.

The process of making the well strips, it was discovered, creates a product that has a surface oxygen content of approximately 0.6%, while plates molded with lubricant and less venting have approximately four times less surface oxygen. Subsequent testing has revealed that an optimal level of surface oxygen exists for creating a substrate that effectively binds or immobilizes aminated DNA.

Figure 3:
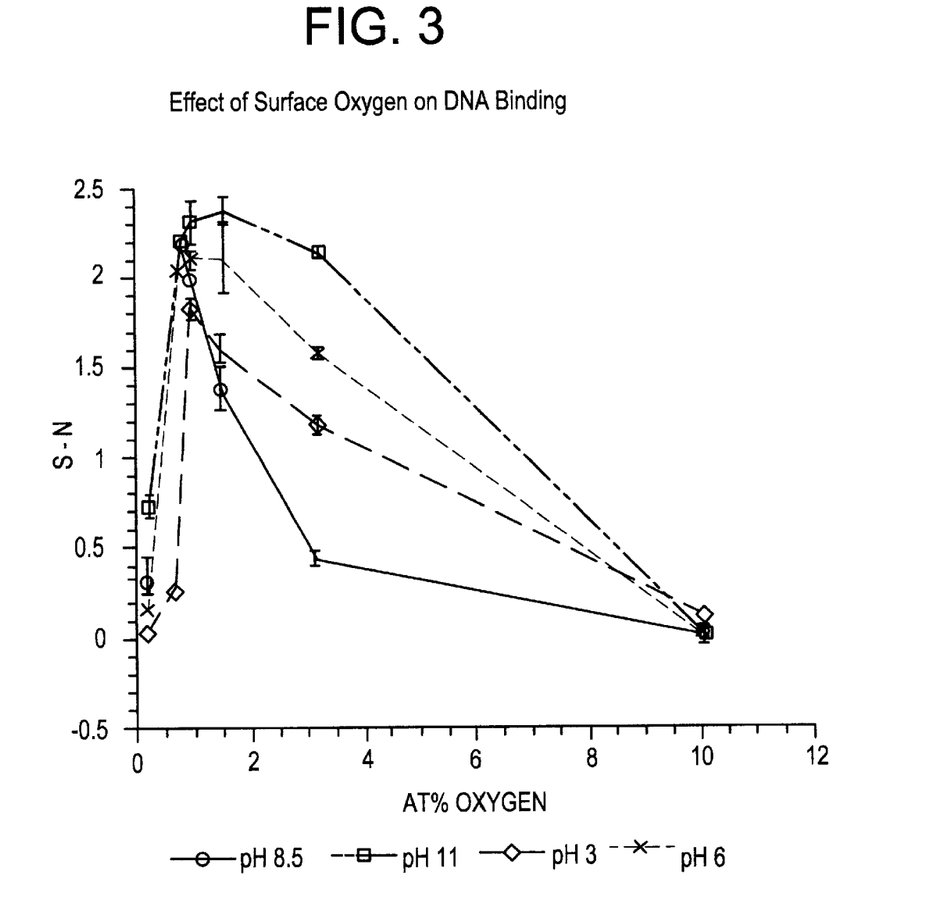
FIG. 3 is a graph of the effect that surface oxygen content of polystyrene has on ability to bind aminated DNA while using binding solutions of varying pH.

FIG. 3 shows the relationship between surface oxygen and ability to bind aminated DNA. The aminated DNA was applied to polystyrene surfaces at a concentration of 1.0 pmol/well in binding solution having four different pH levels, and incubated for 1 hour at 37° C. The ability to bind aminated DNA is measured by the amount of signal received back from a labeled oligonucleotide effectively bound to the surface. These results, which represent averages of readings taken from four different wells, were obtained 20 minutes after adding substrate solution and taken at 405 nm. Table 1 displays the testing results that are plotted in FIG. 3.

TABLE 1

| Substrate | Atomic % Oxygen | Signal pH 3 | Signal pH 6 | Signal pH 8.5 | Signal pH 11 |
| --- | --- | --- | --- | --- | --- |
| Abraded PS Strip | 0.11 | N/A | N/A | 0.32 | N/A |
| Untreated PS Plate | 0.15 | 0.04 | 0.17 | 0.30 | 0.73 |
| Untreated PS Strip | 0.62 | 0.27 | 2.04 | 2.17 | 2.19 |
| Treated PS Plate | 0.81 | 1.83 | 2.10 | 1.99 | 2.31 |

TABLE 1-continued

| Substrate | Atomic % Oxygen | Signal pH 3 | Signal pH 6 | Signal pH 8.5 | Signal pH 11 |
|---|---|---|---|---|---|
| (Treated w/1.5 mRads of Gamma Radiation) High Treated Plate (Treated w/3.0 mRads of Gamma Radiation) | 1.34 | 1.61 | 2.11 | 1.39 | 2.38 |
| High Treated Strip (Treated w/3.0 mRads of Gamma Radiation) | 3.04 | 1.18 | 1.58 | 0.44 | 2.14 |
| Tissue Culture Treated Plate | 10.0 | 0.11 | 0.00 | 0.01 | 0.01 |

As seen from FIG. 3, conditions for binding aminated DNA are optimized in the untreated polystyrene strips at approximately 0.3–2.0 atomic percent, varying slightly depending on the pH of the binding solution. Of the four pH levels surveyed, using an oligo binding buffer having a pH of 11 provided the best binding results at each of the test points.

When the polystyrene strip was abraded so that the surface that contacted the mold was scraped away, both oxygen content and binding ability were decreased, thus substantiating the importance of oxygen on the surface. When polystyrene plates were irradiated with 1.5 mRads of gamma sterilization, the atomic percentage of oxygen and the binding ability of the plates increased significantly. However, when polystyrene is subjected to higher does of gamma radiation, i.e. 3.0 mRads, the surface oxygen content increases, but binding ability tails off. This data suggest an optimum level of surface oxygen content for binding aminated DNA.

It should be noted that although the optimal surface oxygen atomic percentage is approximately between 0.3 and 4.0, binding ability is still enhanced to some degree for surface oxygen atomic percentages between 4.0 and 8.0 when using binding solution having a pH of 3, 6, or 11 as shown in FIG. 3. Additionally, some advantageous binding occurs with polystyrene having a surface oxygen atomic percentage between 0.2 and 0.3. Polystyrene having a binding signal that is below 0.5 has essentially lost its utility as a product for use in assays requiring the immobilization of aminated DNA.

Aside from molding polystyrene products by the process used in making the well strips, surface oxygen content can be increased by several methods known to those skilled in the art. One example is by treatment with appropriate amounts of gamma radiation. Other known methods for affecting surface oxygen content include UV exposure, ozone treatment, and corona discharge. The surface oxygen content can be varied based on intensity and duration of these treatments.

Figure 4:
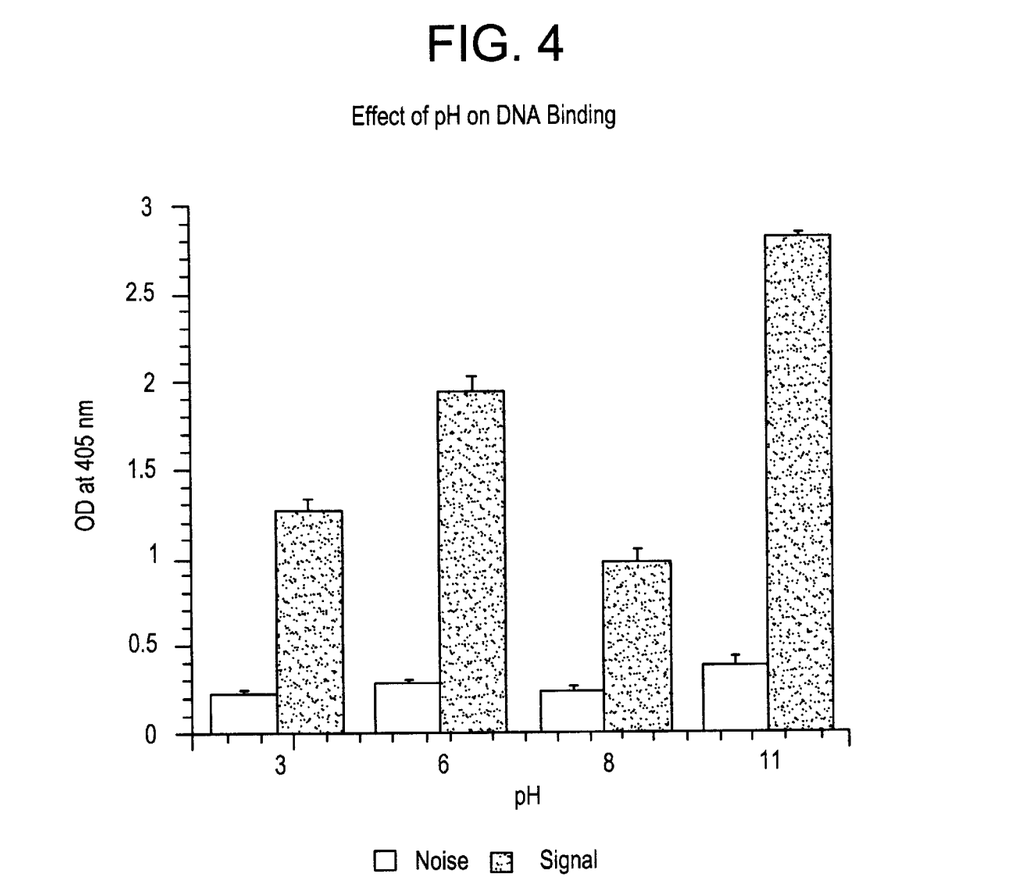
FIG. 4 is a graph of the effects of pH on ability to bind aminated DNA.

FIG. 4 illustrates the effect that pH plays on binding ability of uncoated polystyrene plates having an optimal atomic percentage of surface oxygen. In the experiment that led to the results displayed in FIG. 4, the aminated DNA was applied to plates at a concentration of 1.0 pmol/well and incubated for 1 hour at 37° C. with different pH buffers. The results were obtained 20 minutes after adding fresh substrate solution and readings were taken by OD at 405 nm. The plotted values are averages of results from four different wells. The results indicate that, unlike with surfaces coated with DAS or NOS, aminated DNA will bind to the surface at a variety of pH levels.

Figure 5:
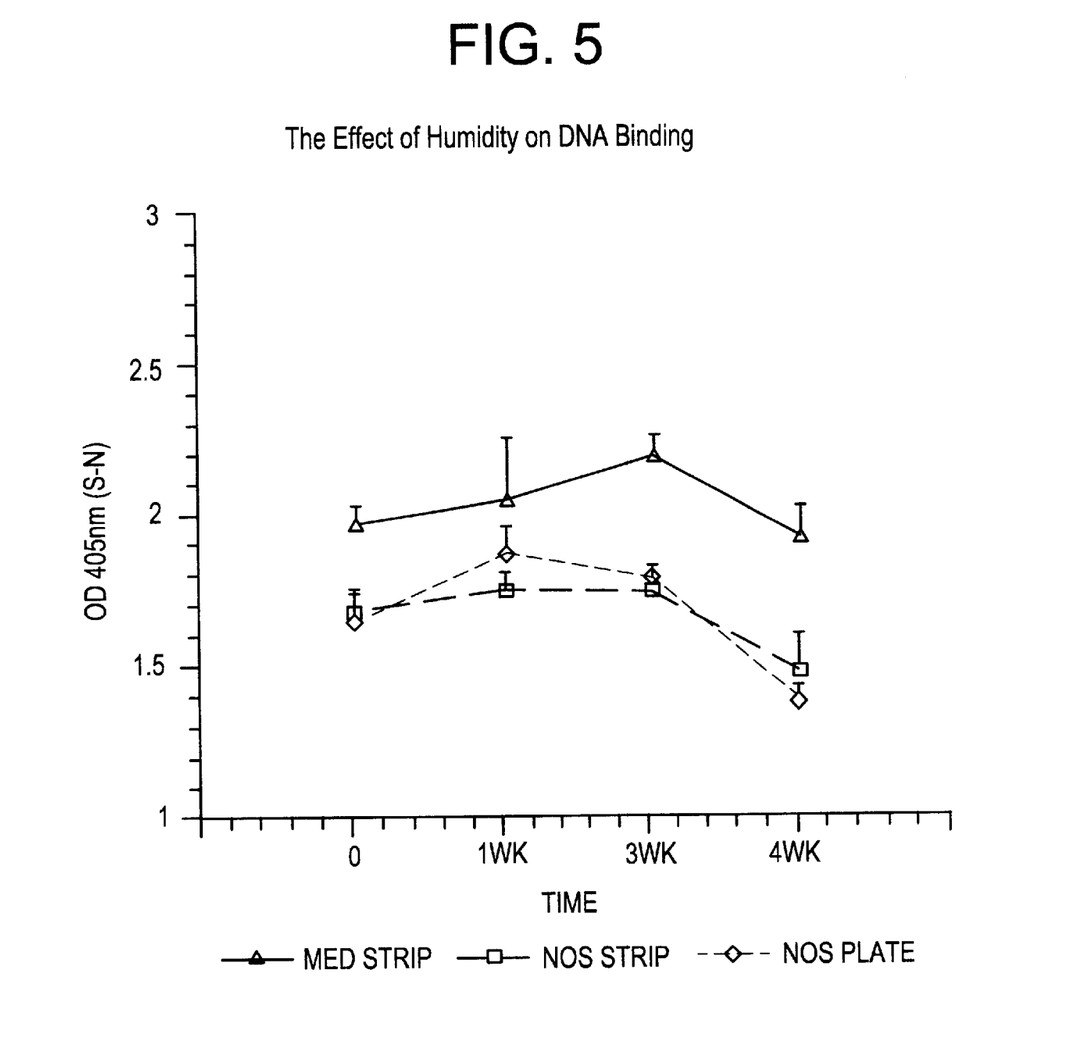
FIG. 5 is a graph of the effects of humidity on ability to bind aminated DNA.

FIG. 5 illustrates the effect that humidity, over a period of time, has on aminated DNA binding. An untreated polystyrene strip and a strip and plate coated with NOS were stored at 85% humidity at 25° C. for up to 4 weeks before the assay. The aminated DNA was applied to the plates at a concentration of 1.0 pmol/well and incubated for 1 hour at 37° C. The results were obtained 20 minutes after adding fresh substrate solution and readings were taken by OD at 405 nm. The plotted values are averages of results from four different wells. As can be seen from FIG. 5, the untreated polystyrene strips bound the aminated DNA better, at each testing point, than the strips coated with NOS.

Data generated indicates further that the linker arm attaching the primary amine to the DNA molecule is essential for DNA binding to untreated polystyrene having surface oxygen atomic percent between 0.3 and 4.0. As used in the experiments described herein, carbon chain molecules of lengths between 6 and 12 carbon atoms were used as linker arms. It has been observed that without the linker arm, less than 25% of signal is obtained when compared to binding results with the linker arm. It has been further observed that the length of the linker arm does not significantly affect DNA binding. This data suggests that the immobilization of aminated DNA on the polystyrene having the optimum surface oxygen content, very likely occurs by chemical or physical bonding between the $NH_2$ and the polystyrene surface. It also eliminates the possibility of a strong contribution of hydrophobic binding between the non-polar carbon-carbon chain in the linker arm and the non-polar polystyrene surface.

The results from the pH experiments, which are displayed graphically in FIG. 4, also shed some light on the binding mechanism between the polystyrene and aminated DNA. The results showed that there were two maxima peaks, at pH 6 and pH 11. This suggests that there might be two different mechanisms involved in the binding of aminated DNA to the surface of polystyrene having a surface oxygen content of between 0.3 and 4.0 atomic percent. The maxima at pH 6 could indicate either physical or chemical bonding—ionic bonding between the $NH_3+$ group on the aminated DNA and carboxylate groups on the oxidized polystyrene surface or chemical reaction between the $NH_2$ group on the aminated DNA and carbonyl groups on the oxidized polystyrene. The pH maxima at pH 11 may be due to chemical bonding between the amine groups on the aminated DNA and the carboxyl groups on the oxidized polystyrene surface.

Nevertheless, knowledge about the mechanisms behind the binding of aminated DNA to the surface of polystyrene having the requisite surface oxygen content is not required to practice the invention.

Figure 6:
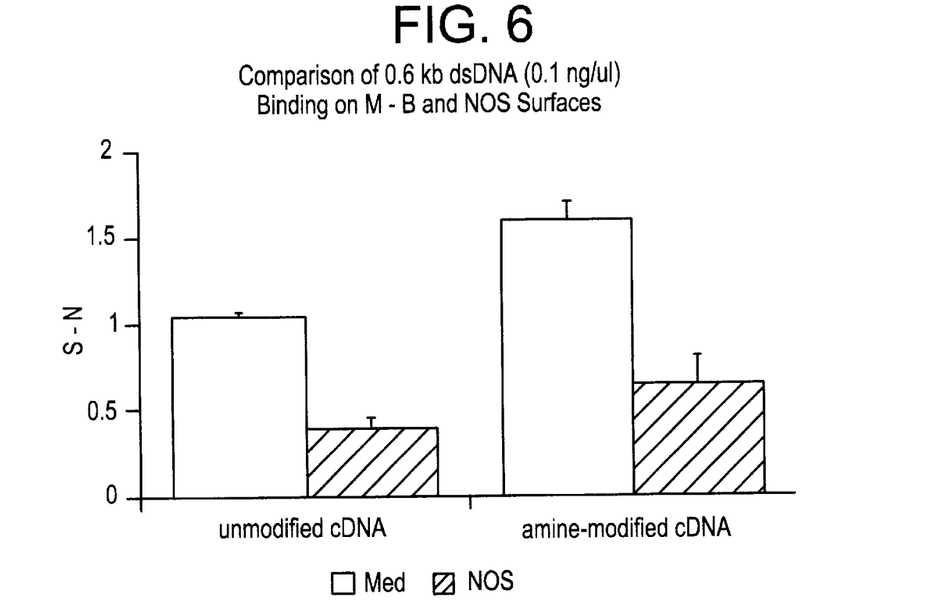
FIG. 6 is a graph comparing the immobilization of both unmodified and amine modified cDNA on oxidized polystyrene and polystyrene coated with NOS.

Further, and as displayed graphically in FIG. 6, polystyrene having a surface oxygen content of 0.62 atomic percent, bound amine modified cDNA significantly better than NOS coated polystyrene or unmodified cDNA when using a binding solution of pH 11. This shows that even aminated DNA strands having greater than 100 nucleotides (cDNA) may be effectively immobilized on polystyrene having an optimum surface oxygen content. Further, even the unmodified cDNA molecules bound to the oxidized polystyrene better than the modified cDNA molecules bound to the NOS coated surface. This perhaps suggests that in the cDNA molecules, amine groups from the numerous individual nucleotides participate in the immobilization.

It should be understood that the binding effects of a polystyrene surface having an optimum level of surface oxygen, as described, is not limited to aminated DNA. The surface is reactive toward amine groups in general. This implies that it is possible to derivitize such reactive polystyrene with various kinds of pendent groups such as carboxyl, amine, biotin, etc. As a result, larger bioreactive molecules such as antigens, antibodies and cell attachment factors may be covalently attached and thereby immobilized to the polystyrene surface. In fact, the reactive polystyrene will react with cell attachment peptides to provide an effective cell growth surface for an endothelial cell line. This approach can also extend to include polyethylene oxide tethered peptides.

One application of the present invention is to pattern polystyrene with alternating cell binding and cell non-binding, or alternating regions of DNA binding and DNA non-binding, in forming an assay array. The individual binding regions may be the subject of independent testing. The alternating regions can be made, for example, by providing polystyrene having non-binding characteristics (surface oxygen content preferably outside of the 0.3–8.0 atomic percent range), and treating only selected portions of the surface to gamma radiation sufficient to create binding characteristics (surface oxygen content preferably between 0.3–4.0 atomic percent). The regions of the surface that are designated as non-binding may be shielded from the radiation by, for example, a patterned mask.

It is also believed that the unique immobilization characteristics shown in relation to surface oxygen content in the range of 0.3–8.0 atomic percent extend to other styrenic polymers such as styrene acrylonitrile copolymer (SAN), ABS (acrylonirile-butadiene-styrene), butadiene-styrene copolymers (HIPS and MIPS, K-resin and Kraton(R)), poly-paramethyl styrene, Styrene-acrylic copolymer, poly alpha methyl styrene, and polymer blends containing styrenic based polymers. The preliminary testing done to date on these polymers has confirmed this belief.

Figure 7:
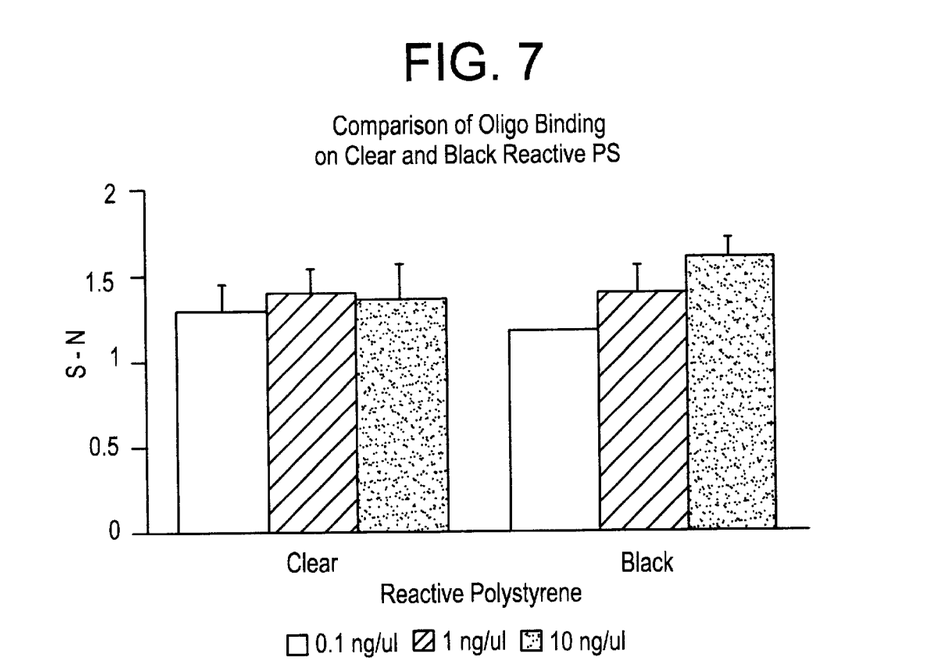
FIG. 7 is a graph comparing the immobilization characteristics of both optically clear and opaque black polystyrene with solutions having varying concentrations of aminated DNA.
Figure 8:
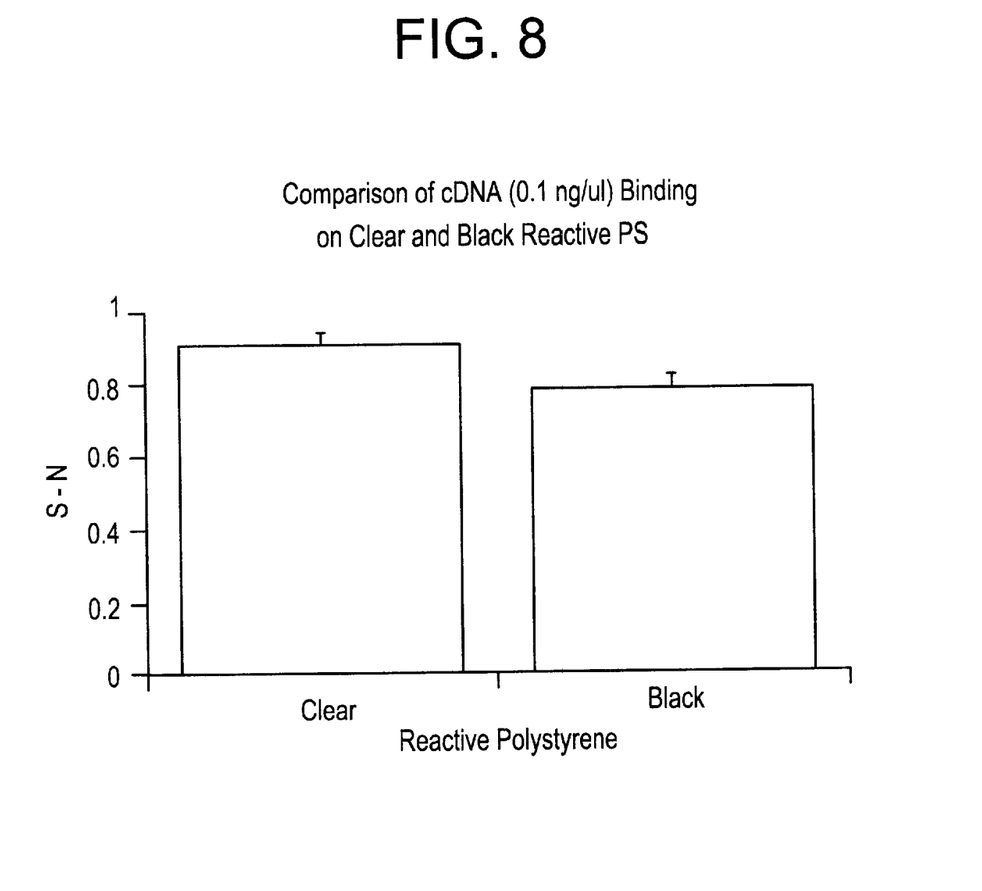
FIG. 8 is a graph comparing aminated cDNA binding on optically clear and opaque black reactive polystyrene.

It should also be noted that optically clear polystyrene having a surface oxygen content of 0.62 atomic percent (MEDIUM BIND), was compared with black opaque styrene-butadiene copolymer (MIPS) having a surface oxygen content of 0.62 atomic percent, for oligonucleotide binding effects. As can be deduced from the immobilization data graphically displayed in FIG. 7 and FIG. 8, no significant difference exists between opaque black and optically clearpolystyrene in its ability to bind aminated DNA or cDNA. What this indicates is that the pigment used in forming the opaque MIPS do not have a detrimental effect on surface binding. This has substantial relevance for the potential use of opaque polystyrenes in chemiluminescent or fluorescent immobilization assays that rely on opaque substrates to limit background noise.

Although the invention has been described in detail for the purpose of illustration, it is understood that such detail is solely for that purpose and variations can be made therein by those skilled in the art, such as modifying the surface oxygen content of other polymers, without departing from the spirit and scope of the invention which is defined by the following claims.

We claim:

1. A method of immobilizing DNA to a surface consisting essentially of:
    a) providing a styrenic polymer substrate having a surface oxygen content of between 0.2 and 8.0 atomic percent, and
    b) attaching at least one aminated DNA molecule directly to the surface of the substrate, said aminated DNA molecule comprising a primary amine attached to a terminal end of a DNA molecule via a linker arm.

2. The method of claim 1 wherein said DNA is an oligonucleotide.

3. The method of claim 1 wherein said DNA is cDNA.

4. The method of claim 1 wherein said styrenic polymer substrate has a surface oxygen content of between 0.3 and 4.0 atomic percent.

5. The method of claim 1 wherein said styrenic polymer substrate has a surface oxygen content of between 0.3 and 2.0 atomic percent.

6. A product for use in chemical and biological analysis consisting essentially of:
    a styrenic polymer substrate having a surface oxygen content of between 0.2 and 8.0 atomic percent; and
    a plurality of aminated DNA molecules directly attached to the surface of said substrate, said aminated DNA molecule comprising a primary amine attached to a terminal end of a DNA molecule via a linker arm.

7. The product of claim 6 wherein said DNA molecules are oligonucleotides.

8. The product of claim 6 wherein said DNA molecules are cDNA.

9. The product of claim 6 wherein said styrenic polymer substrate has a surface oxygen content of between 0.3 and 4.0 atomic percent.

10. The product of claim 6 wherein said styrenic polymer substrate has a surface oxygen content of between 0.3 and 2.0 atomic percent.

11. The product of claim 6 wherein said substrate is a multiwell plate.

12. The product of claim 6 wherein said substrate is a strip of wells.

* * * * *